(12) United States Patent
Fleischer et al.

(10) Patent No.: US 8,920,627 B2
(45) Date of Patent: Dec. 30, 2014

(54) SELECTIVE DETECTOR FOR CARBON MONOXIDE

(75) Inventors: Maximilian Fleischer, Höhenkirchen (DE); Ulrich Hoefer, Oberwil b. Zug (CH); Roland Pohle, Herdweg (DE); Stefan Stegmeier, München (DE)

(73) Assignee: Siemens Aktiengesellschaft, Munich (DE)

( * ) Notice: Subject to any disclaimer, the term of this patent is extended or adjusted under 35 U.S.C. 154(b) by 607 days.

(21) Appl. No.: 13/260,751

(22) PCT Filed: Mar. 30, 2010

(86) PCT No.: PCT/EP2010/054144
§ 371 (c)(1),
(2), (4) Date: Nov. 10, 2011

(87) PCT Pub. No.: WO2010/112476
PCT Pub. Date: Oct. 7, 2010

(65) Prior Publication Data
US 2012/0047995 A1      Mar. 1, 2012

(30) Foreign Application Priority Data
Mar. 31, 2009   (DE) .................. 10 2009 015 121

(51) Int. Cl.
*G01N 27/414* (2006.01)
*G08B 17/117* (2006.01)
*G08B 29/18* (2006.01)
*G01N 33/00* (2006.01)

(52) U.S. Cl.
CPC ............ *G01N 27/414* (2013.01); *G08B 17/117* (2013.01); *G08B 29/185* (2013.01); *G01N 33/0031* (2013.01); *G01N 33/004* (2013.01)
USPC ......................... 205/785.5; 204/424; 257/253

(58) Field of Classification Search
CPC ............ G01N 33/004; G01N 33/0031; G01N 33/0059; G01N 33/0047
See application file for complete search history.

(56) References Cited

U.S. PATENT DOCUMENTS

| 4,792,433 A | 12/1988 | Katsura et al. |
| 5,656,827 A | 8/1997 | Kang et al. |

(Continued)

FOREIGN PATENT DOCUMENTS

| CA | 2375516 A1 | 12/2000 |
| CN | 1997889 A | 7/2007 |

(Continued)

OTHER PUBLICATIONS

JPO computer-generated English language translation of the Claim and Detailed Description of Inoue et al. JP 07-294473 A, patent published Nov. 10, 1995.*

(Continued)

*Primary Examiner* — Alex Noguerola
(74) *Attorney, Agent, or Firm* — Harness, Dickey & Pierce, P.L.C.

(57) ABSTRACT

An embodiment of the invention generally relates to an FET-based detector for carbon monoxide which is based on two sensitive layers. In at least one embodiment, the first of the sensitive layers is catalytically active and therefore reacts equally to alcohols, in particular ethanol, and carbon monoxide. The second of the sensitive layers is not catalytically active and therefore does not react to carbon monoxide, but only to ethanol. The concentration of carbon monoxide can be deduced from the comparison of the signals of the two layers. The two sensitive layers are implemented via similar metal oxide layers, an additional layer having a catalyst such as palladium being provided for the catalytically active layer. Alternatively, two different layers can be used, one of which is already catalytically active without an additional layer.

17 Claims, 2 Drawing Sheets

(56) References Cited

U.S. PATENT DOCUMENTS

2007/0181426 A1     8/2007   Fleischer et al.
2009/0127100 A1     5/2009   Fleischer et al.

FOREIGN PATENT DOCUMENTS

| | | | |
|---|---|---|---|
| DE | 9417289 U1 | 1/1995 | |
| DE | 19701493 C1 | 6/1998 | |
| DE | 102004019638 A1 | 11/2005 | |
| DE | 102005033226 A1 | 1/2007 | |
| DE | 102006046225 A1 | 4/2008 | |
| JP | 58-99747 A * | 6/1983 | ............ G01N 27/58 |
| JP | 02-132358 A * | 5/1990 | ............ G01N 27/12 |
| JP | 07-294473 A * | 11/1995 | ............ G01N 27/12 |
| JP | 200074866 | 3/2000 | |
| JP | 2004317266 A | 11/2004 | |
| RU | 2206083 C1 | 6/2003 | |
| WO | WO 2005103667 A1 | 11/2005 | |
| WO | WO 2007009948 A1 | 1/2007 | |

OTHER PUBLICATIONS

Derwent English language abstract of Murashige et al. JP 02-132358 A, patent published May 21, 1990.*

JPO English language translation of the Abstract of Hiroshi Okamoto JP 58-99747 A, patent published Jun. 14, 1983.*

English langauge translation of the Written Opinion for International application No. PCT/EP2010/054144, orignal dated Sep. 1, 2010.*

Full english langauge translation of Toshihiro Murashige et al. JP 02132358 A, patent publlished May 21, 1990.*

Wu, Yufeng et al; "Research evolution and evolution direction of gas sensors"; Computer measurement and control; vol. 11; No. 10; pp. 731-734; 2003; CN; Oct. 31, 2003.

Siemons M. et at: "Preparation and gas sensing properties of nanocrystalline La-doped CoTiO3", Sensors and Actuators B. 120 (2006) pp. 110-118; Magazine; 2006.

Leu M. et al.: "Evalution of gas mixtures with different sensitive layers incorporated in hybrid fet structures", Sensors and Actuators B, 18-19 (1994), pp. 678-681; Magazine; 1994.

Ivanov P. et al.: "Towards a micro-system for monitoring ethylene in warehouses". Sensors and Actuators B, 111-112 (2005), pp. 63-70; Magazine; 2005.

Lampe U. et al.: "GasFET for the detection of reducing gases", Sensors and Actuators B, Bd. 111-112 (2005), 106-110; Magazine; 2005.

International Search Report for International Application No. PCT/EP2010/054144 dated Mar. 3, 2010.

German Office Action for German Application No. DE 10 2009 015 121.4 dated Dec. 14, 2009.

* cited by examiner

SELECTIVE DETECTOR FOR CARBON MONOXIDE

PRIORITY STATEMENT

This application is the national phase under 35 U.S.C. §371 of PCT International Application No. PCT/EP2010/054144 which has an International filing date of Mar. 30, 2010, which designated the United States of America, and which claims priority on German patent application number DE 10 2009 015 121.4 filed Mar. 31, 2009, the entire contents of each of which are hereby incorporated herein by reference.

FIELD

At least one embodiment of the invention generally relates to a selective detector for carbon monoxide, preferably for indoor applications. At least one embodiment further relates to a method for operating such a detector.

BACKGROUND

The detection of CO (carbon monoxide) in air is extremely relevant to a range of applications in buildings. On the one hand CO is odorless, but at the same time highly toxic. Accordingly, the maximum permissible concentration of CO at the workplace is expressed by an OEL value (OEL=occupational exposure limit) of currently only 30 ppm. If firing plants or flues are thus present in an interior space, conditions of inadequate combustion, i.e. due to lack of air, can result in carbon monoxide occurring in a concentration of several vol. % in the flue gas. If there is a leak in the flue tube or if flue exhaust air escapes into the interior space due to unfavorable pressure conditions—for example as a result of a poorly drawing flue or due to the operation of a fume extraction hood in the vicinity—, toxic CO concentrations can build up. In unfavorable circumstances these can be sufficient to cause damage to health, even leading to death due to poisoning. Thus, for example, in its "Carbon Monoxide Poisoning: Fact Sheet" the Center for Disease Control and Prevention quotes a number of 500 fatalities annually due to CO poisoning for the USA.

Another field of interest with regard to the detection of CO results from the fact that massive amounts of CO are formed in smoldering fires. Apart from the risk to people from poisoning, therefore, the gas can also be used as an indicator of combustion and consequently its detection can also be utilized for early detection of fire situations.

There is therefore a high demand for CO monitoring devices which continuously monitor the ambient air for the occurrence of CO. It is important with regard to the usability of devices of this kind that they provide a reliable warning without giving rise to false alarms. This means that a CO detector must be able to detect the carbon monoxide even when certain other gases are also present in the environment. Such gases are typically odorous gases, for example volatile organic hydrocarbons (VOC), alcohols which escape into the air when alcohol is consumed or from cleaning agents, relative air humidity and oxidizing gases ($NO_2$, $O_3$) infiltrating from the outside air. Fluctuating air temperatures must also not trigger any false alarms.

A known structure for detecting gases is a GasFET, i.e. a field-effect transistor structure embodied for detecting gas. At its gate the GasFET has a particularly gas-sensitive layer. Due to a gas-induced change in the electron work function an additional potential in the order of typically 10-100 mV, which acts as an additional gate voltage on the transistor and can be measured, results at the gas-sensitive layer.

DE 10 2004 019 638 A1 discloses a FET-based CO sensor which is based on a base material having little catalytic activity, for example gallium oxide, which is provided with a catalytically active noble metal dispersion (e.g. Pt or Pd) for the purpose of chemical activation. As a result of the catalytic activation the sensor becomes much more sensitive to CO. A FET-based CO sensor is also known from US 2007/0181426 A1. This sensor is based on a metal oxide as base material and an oxidation catalyst provided thereon. From the same publication it is also known to use the sensor for detecting alcohols or hydrogen.

The CO sensors are extremely cross-sensitive to solvents such as ethanol. Alcohol concentrations of up to several 100 ppm can occur when alcohol-based cleaning agents are used in a building as well as due to spilt alcohol from beverages. These produce the same signal level in the sensor as the CO concentration of 30 ppm that is required to be detected. Consequently incorrect measurements can easily be caused by ethanol.

It is known to provide active carbon filters upstream of a sensor element. The active carbon filters absorb ethanol and allow CO to pass. However, if ethanol is present for a protracted length of time the filter becomes saturated, whereupon it also allows ethanol to pass. Reliable filtering of ethanol is therefore not guaranteed even with active carbon filtering.

SUMMARY

At least one embodiment of the present invention discloses a carbon monoxide sensor which avoids at least one of the above disadvantages or solves at least one of the above problems. The sensor is intended in particular to be capable of reliably detecting carbon monoxide, even when alcohols are present in the ambient air. At least one embodiment further discloses an operating method for such a sensor.

At least one embodiment of the invention is based on the knowledge that when metal-oxide-based sensor layers are used the reaction to CO and the reaction to ethanol are based on different mechanisms of action. Thus, the reaction to CO is a redox reaction which is induced in response to the presence of, in that sense, catalytically active centers. The catalytically active centers can be represented for example by a catalyst dispersion or catalytically active subgroup metal oxides in or on the metal-oxide-based sensor layer. Ethanol, in turn, also reacts at such catalytic centers, though it does not necessarily need these centers. The reaction to ethanol also operates on the basis of an interaction of the —OH group characterizing the alcohols with a catalytically inactive metal oxide.

At least one embodiment of the inventive arrangement for detecting carbon monoxide has a first, catalytically inactive, gas-sensitive layer for detecting concentrations of ethanol. In the arrangement the first gas-sensitive layer is preferably embodied to be capable of detecting ethanol concentrations of less than 1000 ppm, in particular less than 100 ppm ethanol. Furthermore the arrangement has a second, catalytically active, gas-sensitive layer for detecting carbon monoxide concentrations of less than 1000 ppm. The arrangement is embodied to generate at least two processable signals by means of the gas-sensitive layers when exposed to carbon monoxide and/or ethanol.

Thus, in contrast to US 2007/0181426 A1, for example, the arrangement has two sensor layers. In this case the first gas-sensitive layer is not only embodied to detect ethanol, but is also catalytically inactive, i.e. it advantageously detects CO considerably less strongly than the second gas-sensitive layer.

Different implementations come into consideration in each case for the first and second gas-sensitive layers. Thus, the second gas-sensitive layer can include an oxide of a subgroup metal. Examples of this are $La_2O_3$, $CeO_2$, $Mn_2O_3$, $MoO_3$, $TiO_2$, $V_2O_5$. In this case the oxide of the subgroup metal is beneficially the main component of the layer. Preferably the layer includes as far as is technically possible of the oxide of the subgroup metal. Oxides of subgroup metals are catalytically active to such an extent that they permit the detection of carbon monoxide at concentrations of less than 1000 ppm, in particular even less than 100 ppm. In particular the sensitivity is sufficient to allow an alarm threshold in the region of the OEL value of CO, i.e. 30 ppm for example, to be exceeded.

A further possibility for the structure of the second gas-sensitive layer resides in using an oxide of a main group metal. The first gas-sensitive layer then includes an oxide of a main group metal, for example $Ga_2O_3$, $SnO_2$, $In_2O_3$ or $Al_2O_3$. In this arrangement the oxide of the main group metal is beneficially the main component of the second gas-sensitive layer. Preferably the layer includes as far as is technically possible of the oxide of the main group metal. Oxides of main group metals are catalytically inactive to such an extent that they react to CO only at concentrations of far more than 100 ppm. In order to achieve a sensitivity to CO, the second gas-sensitive layer is provided with a dispersion of a catalyst material. Platinum or palladium, for example, can be used for this purpose. Equally, the already aforementioned oxides of subgroup metals can be used, i.e. $La_2O_3$, $CeO_2$, $Mn_2O_3$, $MoO_3$, $TiO_2$, $V_2O_5$, for example.

A third possibility for the structure of the second gas-sensitive layer consists in the second gas-sensitive layer including a catalytically active metal. In this arrangement the catalytically active metal is beneficially the main component of the second gas-sensitive layer. Preferably the layer includes as far as is technically possible of the catalytically active metal.

A possibility for the structure of the first gas-sensitive layer resides in using an oxide of a main group metal. The first gas-sensitive layer then includes an oxide of a main group metal. In this arrangement the oxide of the main group metal is beneficially the main component of the first gas-sensitive layer. Preferably the layer resides as far as is technically possible of the oxide of the main group metal. Oxides of main group metals are catalytically inactive to such an extent that they react to CO only at concentrations of far more than 100 ppm. For the purpose intended here they are therefore practically insensitive to CO. However, they nonetheless react to the presence of ethanol or other alcohols.

It is beneficial if the arrangement includes at least one device for evaluating the signals of the layers which are embodied for determining the carbon monoxide concentration while correcting the effect of alcohol molecules on the measurement. In concrete terms the concentration of carbon monoxide can be determined for example by way of the second gas-sensitive layer. In this case, however, the second gas-sensitive layer is also affected by ethanol or other alcohols in the ambient air. This therefore results in a summation signal which reflects signal components of both substances. The concentration of ethanol or other alcohols is determined by way of the first gas-sensitive layer. Since the first gas-sensitive layer is not affected or only very slightly affected by CO, no CO signal component is contained in its signal. The concentration of ethanol or other alcohols can be computationally eliminated from the summation signal of the second gas-sensitive layer for example by way of a calculation, for example a linear combination of both signals, and the remaining signal expresses the concentration of CO.]

The at least one device beneficially comprises electronics, for example in the form of a microprocessor, for signal pickup, storage and evaluation and for example also for forwarding the acquired information to other points. In this configuration a look-up table can advantageously also be used in which the measurement signals for various combinations of alcohol and CO concentrations are stored for the purpose of determining the CO concentration. This variant has advantages in nonlinear correlations of the signals with the gas concentration.

It is particularly advantageous if the sensor which is formed by the arrangement according to at least one embodiment of the invention is based on a GasFET design. For this purpose two separate field-effect transistor structures are then preferably present. Each of the structures is provided with one of the two gas-sensitive layers on its gate. The signal of the GasFET structures is based on a change in the work function that is induced by gases. A particularly advantageous aspect of this is that even at room temperature the signal is sufficient to allow gas detection. It is also of particular advantage if a so-called SGFET layout, i.e. a suspended-gate structure or a CCFET, i.e. a capacitively controlled FET, is used for the GasFET design. Both are characterized by their hybrid structure, i.e. the gas-sensitive gate and the actual transistor are manufactured separately and joined together by means of a suitable technology. In this way it is possible to incorporate into the transistor as a gas-sensitive layer numerous materials whose conditions of manufacture are not compatible with those of silicon technology, for example. This applies in particular to metal oxides which can be applied using thick- or thin-film technology with subsequent high-temperature processes.

In an advantageous embodiment of the invention the arrangement can include a further sensor which is embodied for determining the relative humidity of the air. By this, it is possible to perform a further correction of the determined CO concentration. The accuracy of the CO measurement is increased as a result, since variations in relative humidity affect the determined CO and ethanol signals.

Preferably the arrangement is embodied such that the operation and the readout of at least the second gas-sensitive layer take place at room temperature. In other words no heating element is used here. In the case of the first layer it is advantageous to provide a heating element.

There are two possibilities for the operation of the heating element. The first possibility resides in keeping the first layer constantly at a temperature slightly higher than room temperature. Beneficial for this purpose are temperatures of 100° C. or less, in particular 80° C. or less. The second possibility consists in heating the sensors intermittently to a higher temperature and allowing the actual measurement operation to be performed at room temperature. For example, the first layer can be heated to 150-200° C. for a period of 5 minutes, the 5 minutes then being followed by a measurement mode of operation of, for example, 1-10 days. The ratio of the duration of the heating period to the duration of the heating-less measurement period is preferably less than 50%, in particular less than 1%. Preferably the sensor layers are operated in principle at temperatures of less than 200° C.

If the sensors are operated by way of thermal activation, then depending on the type of implementation it can last up to a few hours after the thermal activation process until the stable zero point has been established once again at room temperature. In order to bridge the limited measuring accuracy in this phase the sensor system can consist of 2 sensor pairs in which, in alternation, one is operated in the stable measurement mode of operation at room temperature and the other runs through the thermal activation and stabilization process. As an alternative to the full duplication of the sensor arrangement it is also possible, in addition to the individual structure with the preferably unheated second sensor layer, to provide two or more structures with the first sensor layer which are used alternately.

Typical thicknesses of the oxides used lie in the range 0.3-20 µm. Either compact layers, fabricated e.g. using sputter technology or with sol-gel processes using spin coating or spray methods, are used or else porous layers which are fabricated preferably using thick-film technology. In this case the use of porous layers having a large inner surface and hence correspondingly higher reactivity offers the advantage that here higher signals can generally be achieved which can then be read out more easily and more precisely.

BRIEF DESCRIPTION OF THE DRAWINGS

Preferred, yet by no means limiting example embodiments of the invention will now be explained with reference to the drawing. The features are represented schematically therein and corresponding features are labeled with the same reference signs. Specifically, the figures show.

DETAILED DESCRIPTION OF THE EXAMPLE EMBODIMENTS

Figure 1:
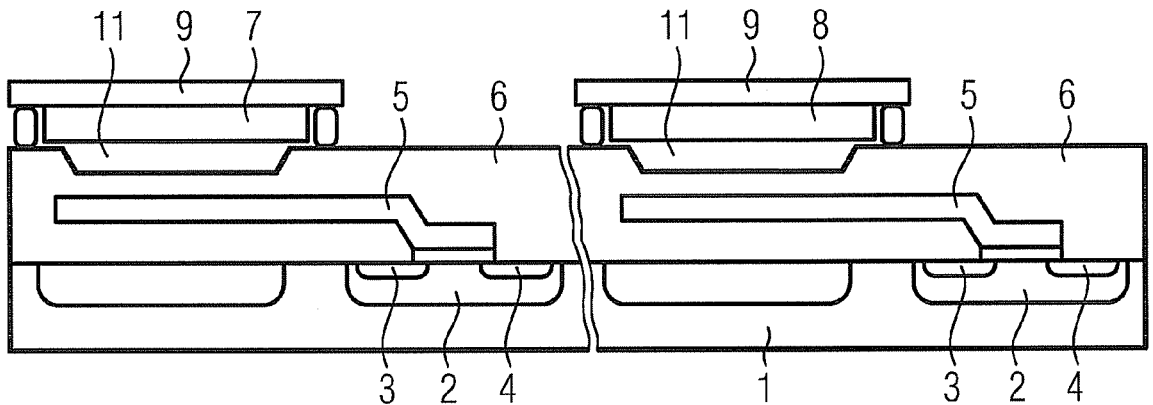
FIG. 1 a CO sensor having two GasFET structures,
FIG. 2 a sensor signal waveform of a catalytically active layer,
FIG. 3 a sensor signal waveform of a catalytically inactive layer, and
FIG. 4 the gas sensitivity of a catalytically inactive layer as a function of the relative air humidity.

The CO sensor according to FIG. 1 is based on a p-silicon substrate 1. In this case the CO sensor has arranged side by side two analogously built field-effect structures. In this arrangement the field-effect structures are typically further away from each other than it would be possible to represent to scale in FIG. 1. Apart from being fabricated on one substrate the sensors can, of course, also be produced on separate substrates and be arranged next to each other on an external carrier, for example a package base or a circuit board.

The field-effect structures are of similar design. They each have a source region 3 and a drain region 4 in an n-Si region 2. Provided thereover is a floating gate 5 inside a passivation layer 6 made of $SiO_2$. The floating gate 5 is covered by the passivation layer 6, a thinned region being provided directly over the floating gate 5. On the thinned region comes the respective sensitive layer 7, 8. In this case the sensitive layers 7, 8 are each carried by a dedicated carrier, the carrier being applied onto the passivation layer 6 in such a way that the sensitive layer 7, 8 is oriented toward the floating gate 5. Together with the passivation layer 6, the sensitive layer 7, 8 then forms—as a result of the thinned region—a channel 11 which permits the influx of gas to the sensitive layer 7, 8.

The first gas-sensitive layer 7 includes gallium oxide ($Ga_2O_3$). The second gas-sensitive layer 8 likewise includes gallium oxide, the second gas-sensitive layer 8 additionally having a catalyst dispersion made of platinum. In this case, therefore, the two gas-sensitive layers 7, 8 includes the same base material, and the second gas-sensitive layer 8 is provided with an additional layer in order to produce a different sensitivity.

Figure 2:
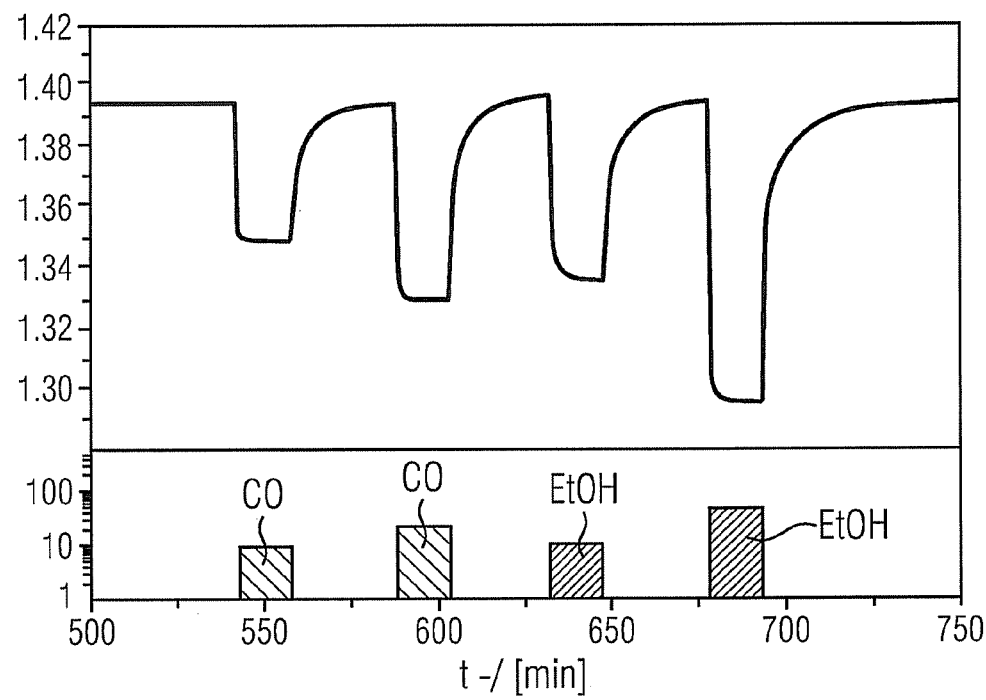
Figure 3:
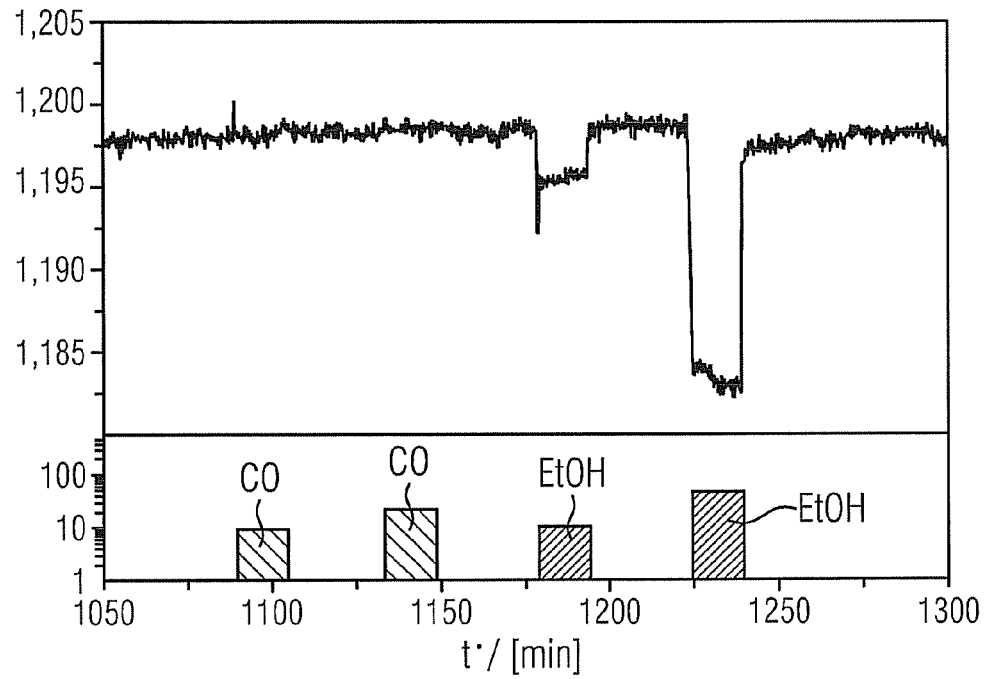

The characteristic curve of the sensor signal of the two discrete sensors of the CO sensor according to FIG. 1 is shown in FIGS. 2 and 3. In this case the first gas-sensitive layer 7 is to be classified as catalytically less active. According to FIG. 3 it consequently exhibits a moderate sensitivity to ethanol (50 ppm), but no visible reaction whatsoever to CO (50 ppm). The second gas-sensitive layer 8, on the other hand, is to be classified as catalytically active on account of the additional platinum layer, as is also evidenced by the sensor reaction according to FIG. 2. The second gas-sensitive layer 8 reveals an approximately 6-times stronger reaction to both gases here than the first gas-sensitive layer 7. In particular a reaction to CO is to be observed here which in its intensity roughly corresponds to the reaction to ethanol.

A linear combination of the sensor signals of the two discrete sensors can therefore be used here to calculate the concentration of CO from the two signals of the individual sensors. It is particularly advantageous in this case that the first gas-sensitive layer 7 effectively does not react at all to CO, thereby making the calculation of the CO concentration considerably more precise than if both sensors were to react. Since the reaction of such gas sensors is typically not a linear function of the concentration, the accuracy of the measurement can be improved through the use of a table containing stored value pairs composed of concentration and measured signal (look-up table).

In this case the first gas-sensitive layer 7 can advantageously be operated at room temperature, i.e. without being heated. This saves energy which in the case of solid-state sensors is mostly required by the heating. For battery-driven sensors, as well as a simplified design, this primarily results in a substantial extension of service life or freedom from maintenance. The second gas-sensitive layer 8, on the other hand, is thermally activated. To that end the second gas-sensitive layer 8 is either briefly thermally activated (120-170° C. for typically 5 min) by a heating device not shown in FIG. 1 and then measured at room temperature or held at a constant temperature of, for example, 80° C. The overall result is very low energy consumption for the CO sensor, thus permitting battery-powered operation, wireless sensor networks or also direct connection to data bus lines.

In the example embodiment illustrated in FIG. 1 the two gas-sensitive layers 7, 8 are built from the same base material. An alternative embodiment variant is produced if the second gas-sensitive layer 8 is constructed instead from a different base material, for example from a catalytically active metal such as platinum. This is to be regarded as catalytically active in respect of the carbon monoxide and enables CO detection without any addition. In this case, therefore, two different base materials are used, but the catalyst dispersion can be omitted.

Figure 4:
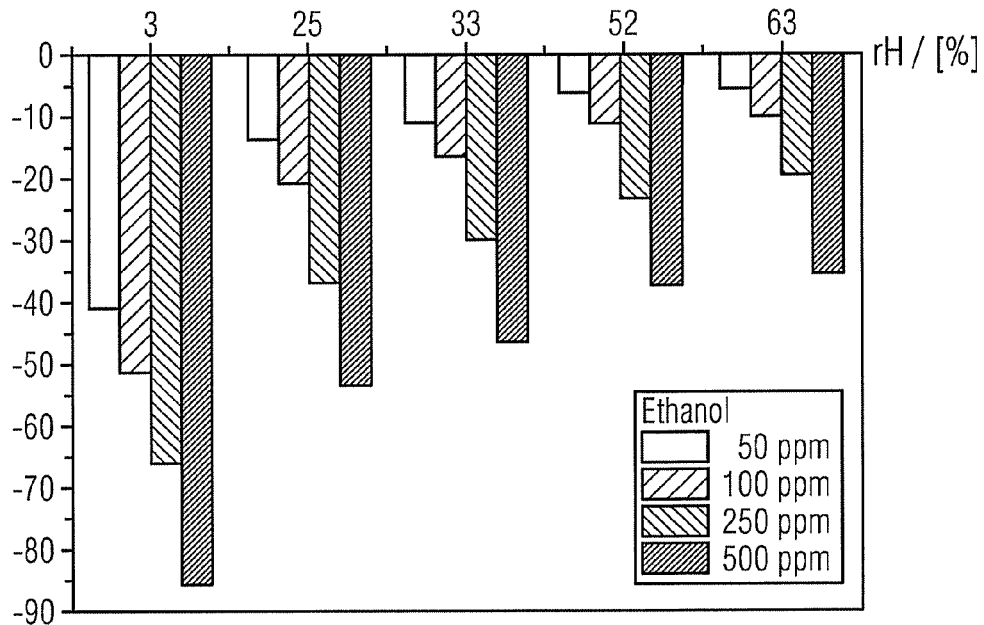

A further sensitivity profile, which is illustrated in FIG. 4, reveals the reaction of the first gas-sensitive layer 7 to ethanol at varying relative humidity. FIG. 4 makes it clear that fluctuating relative humidity has a certain effect on the sensor signal in response to ethanol. This effect can be counteracted by way of an extended CO sensor.

In this case the extended CO sensor has three discrete sensor modules. The first and second sensor module are of similar design in this case and correspond to the simple CO sensor according to the previously described first example embodiment. They therefore have in each case a catalytically active sensor layer and a catalytically inactive sensor layer. Both sensor modules have a gas-sensitive layer made of tin oxide ($SnO2$). This layer can be considered catalytically inactive here, with the result that this sensor essentially reacts to ethanol, but not to CO. Furthermore the gas-sensitive tin oxide layer is also affected by variations in relative humidity. Both sensor modules also have a gas-sensitive layer consisting of MoO3. Since molybdenum oxide is to be regarded as catalytically active, this also reacts to CO as well as to ethanol.

In this example embodiment the simple CO sensors are structured in such a way that an individual heating possibility, for example in the form of a metallic heating loop for the entire substrate 1, is provided for each. In this exemplary embodiment the thermal activation is therefore performed automatically for both layers of a sensor module. For the thermal activation the layers of one of the sensor modules are heated for 5 minutes and then subsequently left unheated for 12 h. In this case it takes up to several hours after the heating process until the properties of the layer are once again at equilibrium. During the settling time a measurement is more difficult. For this reason the gas-sensitive layers of the sensor modules are always heated alternately in the extended CO sensor. Thus, the first sensor module is heated for five minutes and then not used any further for 12 h. During these first 12 h the second sensor module is responsible for the measurements of CO and ethanol. After the 12 h have expired the first sensor module is used for the gas measurements for the next 12 h. During these next 12 h the second sensor module is heated briefly and then left to itself in order to allow a return to equilibrium. At the end of the next 12 h a further switch is made, i.e. the second sensor module is used once again for the CO measurement and the first sensor module is thermally activated.

The third sensor module serves for detecting the relative humidity of the air. Using all of the sensor modules it is therefore possible to determine the CO concentration taking into account effects of ethanol and other alcohols as well as the relative air humidity. In this case the effect of the relative humidity is filtered out in an analogous manner to the correction of ethanol effects. There is thus provided a sensor which, without risk of false alarms due to alcohols—caused by cleaning agents or drinks—, permits a measurement of the carbon monoxide concentration in the region of the OEL value.

The structural variants that have been described with reference to the first and second example embodiment relate to an exclusively CO sensor. It is of course possible to integrate the sensor components into a larger group (array) of sensors which performs other functions in addition to the detection of CO. Thus, for example, the CO detection could be part of a sensor design used for fire detection. In this application of CO detection the carbon monoxide would serve as a precursor gas for detecting smoldering fires. Furthermore the CO sensor could be part of a warning system which also detects other gases such as, for example, natural gas, i.e. methane and ethane, and if necessary emits a warning signal.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:

1. An arrangement for detecting carbon monoxide, comprising two field-effect transistor structures comprising:
a first, catalytically inactive, gas-sensitive layer provided in the region of a first gate of one of the field-effect transistor structures, wherein the first gas-sensitive layer detects ethanol;
a second, catalytically active, gas-sensitive layer provided in the region of a second gate of another of the field-effect transistor structures, wherein the second gas-sensitive layer detects concentrations of carbon monoxide of less than 1000 ppm, and
wherein the arrangement is embodied to generate at least two processible signals by way of the first and second gas-sensitive layers upon exposure to at least one of carbon monoxide and ethanol.

2. The arrangement as claimed in claim 1, further comprising at least one device, embodied to determine the carbon monoxide concentration while correcting the effect of ethanol on the measurement.

3. The arrangement as claimed in claim 1, wherein the first gas-sensitive layer includes an oxide of a main group metal.

4. The arrangement as claimed in claim 3, wherein the oxide is selected from the group consisting of $Ga_2O_3$, $SnO_2$, $In_2O_3$ and $Al_2O_3$.

5. The arrangement as claimed in claim 1, wherein the second gas-sensitive layer includes an oxide of a subgroup metal.

6. The arrangement as claimed in claim 5, wherein the oxide is selected from the group consisting of $La_2O_3$, $CeO_2$, $Mn_2O_3$, $MoO_3$, $TiO_2$, and $V_2O_5$.

7. The arrangement as claimed in claim 1, wherein the second gas-sensitive layer includes a catalytically active metal.

8. The arrangement as claimed in claim 7, wherein the catalytically active metal is platinum or palladium.

9. The arrangement as claimed in claim 1, wherein the second gas-sensitive layer includes an oxide of a main group metal as well as a catalyst dispersion.

10. The arrangement as claimed in claim 1, including a further sensor for determining the relative humidity of air.

11. The arrangement as claimed in claim 1, further comprising means for evaluating the signals, the means being embodied to determine the carbon monoxide concentration while correcting the effect of ethanol on the measurement.

12. A method for operating an arrangement comprising two field-effect transistor structures for detecting carbon monoxide, comprising: a first, catalytically inactive, gas-sensitive layer provided in the region of a first gate of one of the field-effect transistor structures, wherein the first gas-sensitive layer detects ethanol; a second, catalytically active, gas-sensitive layer provided in the region of a second gate of another of the field-effect transistor structures, wherein the second gas-sensitive layer detects concentrations of carbon monoxide of less than 1000 ppm, wherein the arrangement is embodied to generate at least two processable signals by way of the first and second gas-sensitive layers upon exposure to at least one of carbon monoxide and ethanol, wherein the second gas-sensitive layer is heated at least intermittently.

13. The method as claimed in claim 12, wherein the second gas-sensitive layer is heated for the purpose of thermal activation for a first time period and operated unheated for a second time period and is used for the measurement, the ratio of the duration of the first time period to the duration of the second time period being less than 50%.

14. The method as claimed in claim 13, wherein the first gas-sensitive layer is left at room temperature.

15. The method as claimed in claim 12, wherein the second gas-sensitive layer is heated constantly.

16. The method as claimed in claim 15, wherein the first gas-sensitive layer is left at room temperature.

17. The method as claimed in claim 12, wherein the first gas-sensitive layer is left at room temperature.

* * * * *